(12) United States Patent
Warren

(10) Patent No.: US 10,188,447 B2
(45) Date of Patent: Jan. 29, 2019

(54) ELECTROSURGICAL SYSTEM

(71) Applicant: GYRUS MEDICAL LIMITED, Cardiff (GB)

(72) Inventor: Philip John Warren, Rhondda Cynon Taff (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 449 days.

(21) Appl. No.: 14/674,273

(22) Filed: Mar. 31, 2015

(65) Prior Publication Data
US 2015/0282862 A1    Oct. 8, 2015

(30) Foreign Application Priority Data

Apr. 2, 2014    (GB) .................................. 1405889.5

(51) Int. Cl.
*A61B 18/12*    (2006.01)
*A61B 18/04*    (2006.01)
(Continued)

(52) U.S. Cl.
CPC ........ *A61B 18/1206* (2013.01); *A61B 18/042* (2013.01); *H01R 13/04* (2013.01);
(Continued)

(58) Field of Classification Search
CPC .............. A61B 18/042; A61B 18/1206; A61B 2017/00477; A61B 2018/00178; A61B 2018/122
See application file for complete search history.

(56) References Cited

U.S. PATENT DOCUMENTS 4,901,719 A    2/1990  Trenconsky et al.
5,268,592 A   12/1993  Bellamy et al.
(Continued)

FOREIGN PATENT DOCUMENTS

CN    1665451 A    9/2005
CN  103378443 A   10/2013
(Continued)

OTHER PUBLICATIONS

Search Report Under Section 17(5), dated Oct. 16, 2014, for UK Application No. GB1405889.5.
(Continued)

*Primary Examiner* — Daniel Fowler
*Assistant Examiner* — Tigist Demie
(74) *Attorney, Agent, or Firm* — Oliff PLC

(57) ABSTRACT

A connection system for an electrosurgical instrument comprises first and second connectors capable of being mated one with the other, the first connector (5) being associated with an electrosurgical generator (1) and the second connector (12) being associated with the electrosurgical instrument (9). The first and second connectors each include at least three connector components, each of the three connector components of the first connector (5) being capable of being connected and disconnected to a to respective one of the three connector components of the second connector (12). When the first connector components (14, 19) are connected to each other they are capable of delivering an RF energy output from the electrosurgical generator (1) to the electrosurgical instrument (9). When the second connector components (16, 22) are connected to each other they are capable of delivering a supply of ionizable gas to the electrosurgical instrument (9). When the third connector components (15, 21) are connected to each other they capable of identifying the electrosurgical instrument (9) to (Continued)

the electrosurgical generator (1). When the first and second connectors are mated one with the other, the third connector components (15, 21) are connected one to the other only after the first and second connector components are connected one to the other.

6 Claims, 2 Drawing Sheets

(51) Int. Cl.
  *H01R 13/04* (2006.01)
  *A61B 18/00* (2006.01)
  *H01R 13/00* (2006.01)
  *A61B 17/00* (2006.01)

(52) U.S. Cl.
  CPC ........... *A61B 2017/00477* (2013.01); *A61B 2018/00178* (2013.01); *A61B 2018/122* (2013.01); *H01R 13/005* (2013.01); *H01R 2201/12* (2013.01)

(56) References Cited

U.S. PATENT DOCUMENTS

| | | | |
|---|---|---|---|
| 6,905,362 B2 | 6/2005 | Williams | |
| 7,235,071 B2 | 6/2007 | Gonnering | |
| 7,311,707 B2 | 12/2007 | Hagg et al. | |
| 2004/0030330 A1* | 2/2004 | Brassell | A61B 18/1206 606/41 |
| 2005/0240172 A1* | 10/2005 | Hagg | A61B 18/042 606/32 |
| 2010/0305563 A1* | 12/2010 | Varney | A61B 18/14 606/41 |
| 2011/0045680 A1* | 2/2011 | Beller | A61B 18/14 439/188 |
| 2012/0283732 A1* | 11/2012 | Lam | A61B 17/00491 606/49 |
| 2013/0214527 A1 | 8/2013 | Gro | |
| 2013/0288500 A1* | 10/2013 | Munkelt | H01R 13/15 439/246 |

FOREIGN PATENT DOCUMENTS

| | | |
|---|---|---|
| EP | 1764057 A1 | 4/2009 |
| JP | 2002-280119 A | 9/2002 |
| JP | 2005-530573 A | 10/2005 |
| JP | 2008-253464 A | 10/2008 |
| JP | 2013-509979 A | 3/2013 |
| JP | 2013-229329 A | 11/2013 |
| WO | 2010/091811 | 8/2010 |

OTHER PUBLICATIONS

Sep. 4, 2018 Office Action issued in Chinese Patent Application No. 201510223967.0.

Nov. 13, 2018 Office Action issued in Japanese Patent Application No. 2015-705547.

\* cited by examiner

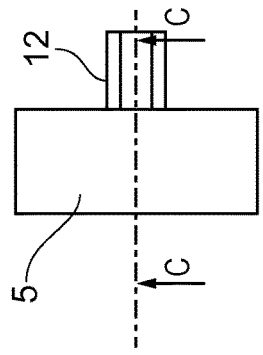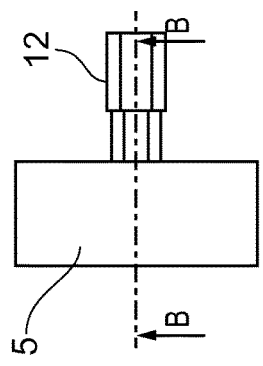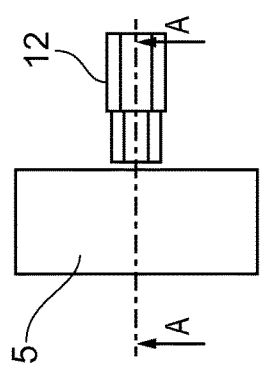
FIG. 2A
FIG. 3A
FIG. 4A
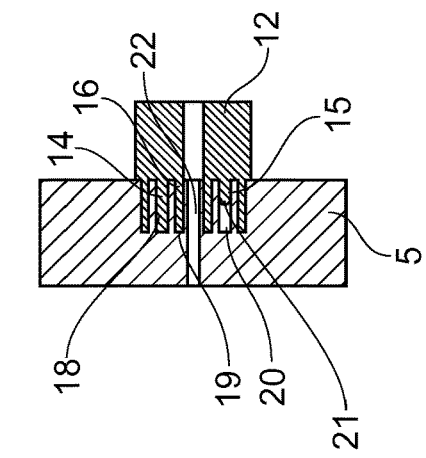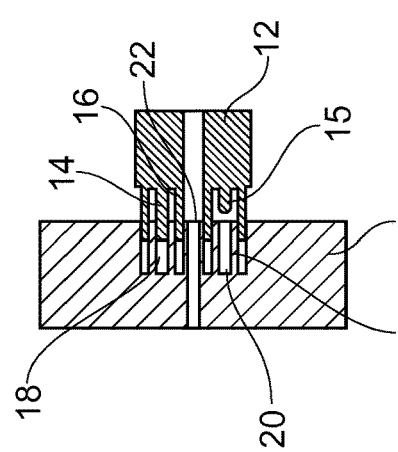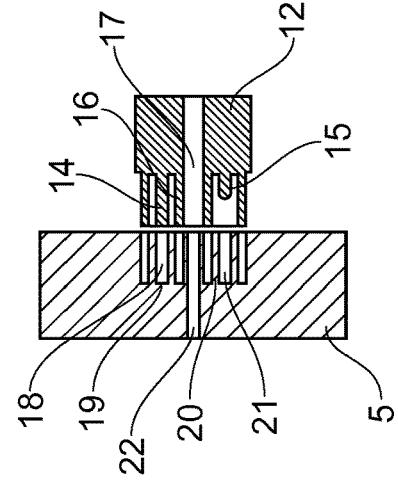
FIG. 2B
FIG. 3B
FIG. 4B

ELECTROSURGICAL SYSTEM

This application claims priority to United Kingdom Application No. 1405889.5, filed 2 Apr. 2014, the entire contents of which are incorporated herein by reference.

FIELD OF THE INVENTION

Embodiments of the invention relate to an electrosurgical system and in particular to the non-contact treatment of tissue using an ionisable gas such as argon.

BACKGROUND TO THE INVENTION

Argon beam coagulators have been known for many years, and examples are given in U.S. Pat. Nos. 4,040,426, 6,039,736 and 6,197,026. The first example is an end-effect instrument, in which the ionised gas exits through the end of the instrument, while the latter two examples are directed at side-effect instruments, in which the ionised gas exits the instrument though an aperture in the side of the instrument. Such instruments are often referred to as APC instruments (Argon Plasma Coagulation).

APC systems require the supply of both an ionisable gas and also RF energy to ionise the gas. U.S. Pat. No. 7,311,707 describes a connector device for an APC system, with connections for both RF energy and a gas supply.

SUMMARY OF THE INVENTION

Embodiments of the present invention attempt to provide an improvement to the above described type of connector system, such that the operation of the system can be inhibited in the event of a partial or incorrect connection of the RF energy or ionisable gas connections.

Accordingly, from one aspect a connection system is provided for an electrosurgical instrument, comprising first and second connectors capable of being mated one with the other, the first connector being associated with an electrosurgical generator and the second connector being associated with the electrosurgical instrument, wherein the first and second connectors each include at least three connector components, each of the three connector components of the first connector being capable of being connected and disconnected to a respective one of the three connector components of the second connector, the arrangement being such that when the first connector components are connected to each other they are capable of delivering an RF energy output from the electrosurgical generator to the electrosurgical instrument, and when the second connector components are connected to each other they are capable of delivering a supply of ionisable gas to the electrosurgical instrument, and when the third connector components are connected to each other they capable of identifying the electrosurgical instrument to the electrosurgical generator, characterised in that the first and second connectors are designed such that when they are mated one with the other, the third connector components are connected one to the other only after the first and second connector components are connected one to the other.

The provision of the third connector components allows for the electrosurgical instrument to be identified to the electrosurgical generator. This can be achieved by various means, including the interrogation of an electronic component such as an EEPROM present within the instrument, or the completion of a circuit including a passive electrical identification component such as a resistor or capacitor present within the instrument. Whichever method is employed, the connection of the third connector components allows for the identification of the instrument to the electrosurgical generator.

The arrangement of the connector components such that the third connector components are connected only after the first and second connector components means that the instrument is identified only once the RF energy and ionisable gas supply connections have been properly established. In this way, the generator can be programmed such that the RF energy and ionisable gas supplies are inhibited until after the successful identification of the instrument. This means that situations can be avoided in which the RF energy is activated before the ionisable gas connection has been properly established, or conversely the ionisable gas is supplied before the RF energy connection has been properly established. Only once the instrument has been identified, meaning that the third connector components are connected one to the other, there is confidence that the RF energy and ionisable gas connections have been established, as these take place before the third connector components are connected.

Typically, the third connection component on the first connector is set back axially with respect to at least one of the first and second connection components on the first connector. Conveniently, the third connection component on the first connector is set back axially with respect to both the first and second connection components on the first connector. Additionally or alternatively, the third connection component on the second connector is set back axially with respect to at least one of the first and second connection components on the second connector. In this case the third connection component on the second connector is conceivably set back axially with respect to both the first and second connection components on the second connector.

According to a preferred arrangement, one of the first connection components comprises a pin, and the other of the first connection components comprises a socket adapted to receive the pin. Typically, one of the third connection components to comprises a pin, and the other of the third connection components comprises a socket adapted to receive the pin. Conveniently, one of the second connection components comprises a nozzle, and the other of the second connection components comprises a tube in which the nozzle can be received.

The first connector preferably comprises the first, second, and third connection components housed within a unitary housing. Typically, the second connector also comprises the first, second and third connection components housed within a unitary housing.

Embodiments of the invention further reside in an electrosurgical system comprising an electrosurgical generator, a source of ionisable gas, a controller and an electrosurgical instrument, the electrosurgical generator including a source of RF energy, the system also including a first connector and the electrosurgical instrument including a second connector, the first and second connectors being capable of being mated one with the other, wherein the first and second connectors each include at least three connector components, each of the three connector components of the first connector being capable of being connected and disconnected to a respective one of the three connector components of the second connector, the arrangement being such that when the first connector components are connected to each other the electrosurgical generator is capable of delivering an RF energy output from the source of RF energy to the electrosurgical instrument, and when the second connector components are connected to each other the source of ionisable gas is capable of delivering a supply of ionisable gas to the electrosurgical instrument, and when the third connector components are connected to each other the controller is capable of identifying the electrosurgical instrument, characterised in that the first and second connectors are designed such that when they are mated one with the other, the third connector components are connected one to the other only after the first and second connector components are connected one to the other.

Preferably, the controller is adapted to inhibit the supply of RF energy until after the controller has successfully identified the electrosurgical instrument. Typically, the controller is also adapted to inhibit the supply of ionisable gas until after the controller has successfully identified the electrosurgical instrument. As described previously, this means that situations can be avoided in which the RF energy is to activated before the ionisable gas connection has been properly established, or conversely the ionisable gas is supplied before the RF energy connection has been properly established.

Typically, the controller is present within the electrosurgical generator. Furthermore, the source of ionisable gas is conceivably present within the electrosurgical generator. However, the source of ionisable gas can alternatively be provided as a separate unit, with connections from both the electrosurgical generator and the source of ionisable gas leading to the first connector.

From a further aspect, some embodiments of the invention also provide a method of operating an electrosurgical system, the system comprising an electrosurgical generator, a source of ionisable gas, and an electrosurgical instrument, the electrosurgical generator including a source of RF energy, the system also including a first connector and the electrosurgical instrument including a second connector, the method comprising: presenting the first and second connectors for mating; mating the first and second connectors such that respective first and second connector components of the first and second connectors form respective first and second connections before respective third connector components of the first and second connectors form a third connection; after the respective third connector components are connected, identifying the electrosurgical instrument via the third connection between the third connector components; and in dependence on the identification of the electrosurgical instrument, supplying ionisable gas to the electrosurgical instrument via the second connection and supplying RF energy to the electrosurgical instrument via the first connection.

DESCRIPTION OF THE DRAWINGS

An embodiment of the invention will now be further described, by way of example only, with reference to the accompanying drawings, in which:

FIG. 2A is an enlarged side view of the plug and socket of FIG. 1, presented one to the other, FIG. 2B is a sectional view of the plug and socket of FIG. 2A, taken through the line A-A of FIG. 2A, FIG. 3A is a side view of the plug and socket of FIG. 1, shown in a partially engaged position, FIG. 3B is a sectional view of the plug and socket of FIG. 3A, taken through the line B-B of FIG. 3A, FIG. 4A is a side view of the plug and socket of FIG. 1, shown in a fully engaged position, FIG. 4B is a sectional view of the plug and socket of FIG. 4A, taken through the line C-C of FIG. 4A.

DESCRIPTION OF THE EMBODIMENTS

Figure 1:
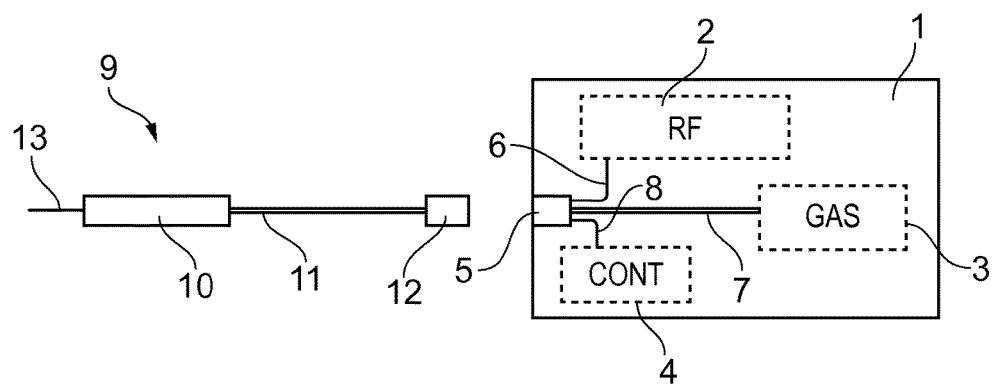
FIG. 1 is a schematic view of an electrosurgical system in accordance with an embodiment of the present invention.

Referring to FIG. 1, an electrosurgical system comprises an electrosurgical generator 1 containing a source of RF energy 2, a supply of ionisable gas 3 and a controller 4. The RF source 2 is connected to a socket 5 by means of a line 6, the gas supply 3 is connected to the socket 5 by means of supply hose 7, and the controller 4 is connected to the socket 5 by means of line 8. The socket 5 constitutes a first connector.

An APC instrument is shown generally at 9, and consists of an instrument body 10, supply cord 11, and a plug 12 which constitutes a second connector. The instrument 9 also includes an electrode 13. When the plug 12 is inserted into the socket 5 and the instrument is activated, argon gas is supplied to the distal end of the instrument body 10, and ionised by the electrode 13 which is energised by the RF source 2.

FIGS. 2A & 2B show the plug 12 and socket 5 in more detail. Plug 12 includes an RF pin 14 connected via a lead (not shown) to the electrode 13. The plug also includes an ID pin 15 connected to an identification element (not shown) such as an EEPROM. The plug 12 also includes a gas connector in the form of a hose 16 defining a gas lumen 17. The ID pin 15 is shorter than the RF pin 14, and also set back with respect to the end of the hose 16.

The socket 5 includes a first receptacle 18 for the RF pin, the first receptacle including an RF contact 19 in communication with the RF source 2 via line 6. The plug 5 also includes a second receptacle 20 for the ID pin, the second receptacle including an to ID contact 21 in communication with the controller 4 via line 8. Finally, the plug 5 includes a nozzle 22 in communication with the gas supply 3 via the supply hose 7. FIGS. 2A & 2B show the plug 12 being presented to the socket 5.

FIGS. 3A & 3B shown the plug 12 partially inserted within socket 5. The RF pin 14 is received within the first receptacle 18, and the hose 16 is fitting over the nozzle 22. However, the ID pin 15 is not yet received in the second receptacle 20, and so is not yet making contact with the ID contact 21. In this position, the controller 4 is unable to establish contact with the EEPROM, and so the controller sends signals to the RF source 2 and the gas supply 3 inhibiting their operation as the connections for the supply of argon and RF energy to the instrument 9 are deemed insufficiently secure.

Finally, FIGS. 4A & 4B show the plug 12 fully inserted within the socket 5. The RF pin 14 is fully received within the first receptacle 18 so as to make proper contact with the RF contact 19, and the hose 16 is fully fitted over the nozzle 22. In this position the ID pin 15 is now received in the second receptacle 20, and makes contact with the ID contact 21. The controller 4 is able to establish contact with the EEPROM, and so the controller identifies the instrument 9 and that the connections for the supply of argon and RF energy to the instrument 9 are deemed sufficiently secure. Accordingly, the controller 4 sends signals to the RF source 2 and the gas supply 3 to authorise their operation to supply RF energy and argon gas respectively to the instrument 9.

The shorter ID pin 15 ensures that contact is only made with the ID contact 21 once the RF and gas supply connections have been firmly established. In this way, RF energy cannot be activated without a proper gas connection, and similarly argon gas cannot be supplied without a proper RF connection.

Figure 5:
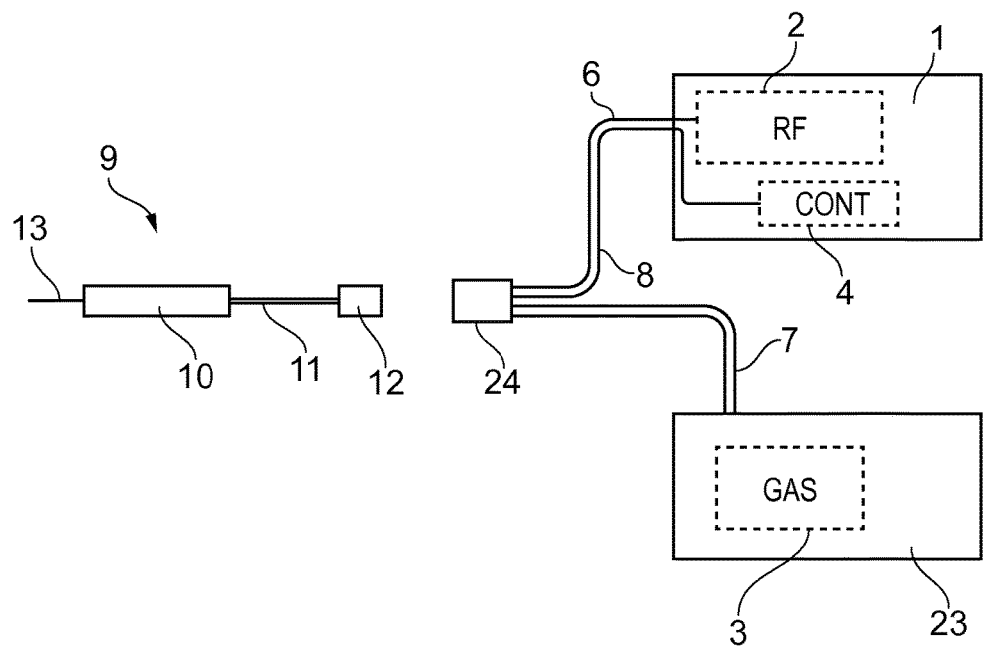
FIG. 5 is a schematic view of an electrosurgical system in accordance with an alternative embodiment of the present invention.

While FIG. 1 shows the RF source 2, gas supply 3 and controller 4 within the generator 1, FIG. 5 shows an alternative arrangement. RF source 2 and controller 4 are in the generator 1 as before, but the gas supply 3 is in a separate gas unit 23. The generator no longer has a socket 5, but instead the RF source 2 is connected to an external connector 24, once again by means of line 6. The controller 4 is also connected to the external connector 24, this time by means of line 8. The gas unit 23 has a separate connection to the external connector 24, by means of supply hose 7. The inputs to the external connector 24, in the form of line 6, line 8 and hose 7, are in the to form of sub-connectors (not shown), to allow the generator 1 and gas unit 23 to be transported separately.

The external connector 24 constitutes a first connector, and a plug 12 exactly as previously described constitutes a second connector. The APC instrument 9 is as previously described. The plug 12 and connector 24 are similar to those described with reference for FIGS. 2 to 4, with the external connector 24 taking the place of the socket 5. As before, the ID pin 15 is shorter than the RF pin 14 or hose 16, such that the ID connection is only established once the RF and gas connections are firmly in place.

Those skilled in the art will appreciate that many variations may be made without departing from the scope of the present invention. For example, although the embodiments of FIGS. 2 to 4 are described with the ID pin 15 being shorter than the RF pin 14 or hose 16, the same effect can be achieved by having the ID pin 15 the same length as the other components but positioning the ID contact 21 so that it is further back within the second receptacle 20. Any arrangement in which the ID pin 15 makes a connection with the ID contact 21 only after the other components are fully engaged will achieve the desired effect.

The above embodiments are described as having a single RF pin 14 and RF contact 19, as would typically be the case for a monopolar RF system. However, those skilled in the art will appreciate that a bipolar RF system can be utilised (with first and second RF pins, and first and second RF contacts), without departing from the scope of the present invention. The recognition that the first and second connectors each include "at least three" connector components allows for either monopolar or bipolar RF systems to be incorporated.

The invention claimed is:
1. An electrosurgical system comprising:
an electrosurgical generator;
a source of ionisable gas;
a controller; and
an electrosurgical instrument, the electrosurgical generator including a source of RF energy, the system also including a first connector and the electrosurgical instrument including a second connector,
the first connector being configured to connect with the second connector,
the first connector comprising a first set of at least three connector components,
the second connector comprising a second set of at least three connector components,
each of the three connector components of the first set being configured to connect to and disconnect from a respective one of the at least three connector components of the second set,
a connection between the first connector component of the first set and the first connector component of the second set is configured to allow the electrosurgical generator to deliver an RF energy output from the source of RF energy to the electrosurgical instrument,
a connection between the second connector component of the first set and the second connector component of the second set is configured to allow the source of ionisable gas to deliver a supply of ionisable gas to the electrosurgical instrument,
a connection between the third connector component of the first set and the third connector component of the second set is configured to allow the controller to identify the electrosurgical instrument, and
the third connector component of the first set being configured to connect to the third connector component of the second set only after the first connector component of the first set is connected to the first connector component of the second set and the second connector component of the first set is connected to the second connector component of the second set, wherein the controller is adapted to inhibit the supply of RF energy until after the controller has successfully identified the electrosurgical instrument.

2. An electrosurgical system according to claim 1, wherein the controller is present within the electrosurgical generator.

3. An electrosurgical system according to claim 1, wherein the source of ionisable gas is present within the electrosurgical generator.

4. A method of operating an electrosurgical system, the system comprising an electrosurgical generator, a source of ionisable gas, and an electrosurgical instrument, the electrosurgical generator including a source of RF energy, the system also including a first connector and the electrosurgical instrument including a second connector, the method comprising:
presenting the first and second connectors for mating;
mating the first and second connectors such that respective first and second connector components of the first and second connectors form respective first and second connections before respective third connector components of the first and second connectors form a third connection;
after the respective third connector components are connected, identifying the electrosurgical instrument via the third connection between the third connector components; and
supplying ionisable gas to the electrosurgical instrument from the source of ionisable gas via the second connection and supplying RF energy to the electrosurgical instrument from the source of RF energy via the first connection when the electrosurgical instrument has been identified.

5. An electrosurgical system comprising:
an electrosurgical generator;
a source of ionisable gas;
a controller; and
an electrosurgical instrument, the electrosurgical generator including a source of RF energy, the system also including a first connector and the electrosurgical instrument including a second connector,
the first connector being configured to connect with the second connector, the first connector comprising a first set of at least three connector components, the second connector comprising a second set of at least three connector components, each of the three connector components of the first set being configured to connect to and disconnect from a respective one of the at least three connector components of the second set, a connection between the first connector component of the first set and the first connector component of the second set is configured to allow the electrosurgical generator deliver an RF energy output from the source of RF energy to the electrosurgical instrument, a connection between the second connector component of the first set and the second connector component of the second set is configured to allow the source of ionisable gas deliver a supply of ionisable gas to the electrosurgical instrument, a connection between the third connector component of the first set and the third connector component of the second set is configured to allow the controller to identify the electrosurgical instrument, the third connector component of the first set being configured to connect to the third connector component of the second set only after the first connector component of the first set is connected to the first connector component of the second set and the second connector component of the first set is connected to the second connector component of the second set;

the controller being adapted to inhibit the supply of RF energy and the supply of ionisable gas until after the controller has successfully identified the electrosurgical instrument.

6. An electrosurgical system comprising:
an electrosurgical generator;
a source of ionisable gas;
a controller; and
an electrosurgical instrument, the electrosurgical generator including a source of RF energy, the system also including a first connector and the electrosurgical instrument including a second connector, the first connector being configured to connect with the second connector, the first connector comprising a first set of at least three connector components, the second connector comprising a second set of at least three connector components, each of the three connector components of the first set being configured to connect to and disconnect from a respective one of the at least three connector components of the second set, when the first connector component of the first set is connected to the first connector component of the second set, the electrosurgical generator is being configured to deliver an RF energy output from the source of RF energy to the electrosurgical instrument, a connection between the second connector component of the first set and the second connector component of the second set is configured to allow the source of ionisable gas to deliver a supply of ionisable gas to the electrosurgical instrument, a connection between the third connector component of the first set is and the third connector component of the second set is configured to allow the controller to identify the electrosurgical instrument, and the third connector component of the first set being configured to connect to the third connector component of the second set only after the first connector component of the first set is connected to the first connector component of the second set and the second connector component of the first set is connected to the second connector component of the second set, wherein the controller is adapted to inhibit the supply of ionisable gas until after the controller has successfully identified the electrosurgical instrument.

* * * * *